(12) United States Patent
Chevallet et al.

(10) Patent No.: US 7,517,387 B2
(45) Date of Patent: Apr. 14, 2009

(54) GAS SEPARATION DEVICES

(75) Inventors: Jacques Chevallet, Serezin du Rhone (FR); Nicolas Semenzato, Lyons (FR); Alain Frugier, Tignieu (FR); Francesco Ribolzi, Modena (IT)

(73) Assignee: Gambro Lundia AB (SE)

( * ) Notice: Subject to any disclaimer, the term of this patent is extended or adjusted under 35 U.S.C. 154(b) by 557 days.

(21) Appl. No.: 10/518,787

(22) PCT Filed: May 26, 2003

(86) PCT No.: PCT/IB03/02281

§ 371 (c)(1),
(2), (4) Date: Jun. 16, 2005

(87) PCT Pub. No.: WO04/000391

PCT Pub. Date: Dec. 31, 2003

(65) Prior Publication Data

US 2005/0247203 A1    Nov. 10, 2005

(30) Foreign Application Priority Data

Jun. 24, 2002  (IT)  ............................ MI2002A1389
Jun. 24, 2002  (IT)  ............................ MI2002A1390

(51) Int. Cl.
*B01D 19/00* (2006.01)

(52) U.S. Cl. ................... 95/24; 95/261; 96/209; 96/166; 96/211; 96/212; 604/5.04; 604/122; 210/512.1

(58) Field of Classification Search .................... 95/261, 95/19, 24; 96/209, 166, 211, 212, 174; 604/5.04, 604/122; 210/512.1
See application file for complete search history.

(56) References Cited

U.S. PATENT DOCUMENTS

| 2,758,597 A | 8/1956 | Elder |
| 3,631,654 A | 1/1972 | Riely |
| 3,677,248 A | 7/1972 | McPhee |
| 3,778,971 A | 12/1973 | Granger et al. |

(Continued)

FOREIGN PATENT DOCUMENTS

| AU | 744404 | 1/1999 |
| CA | 1311694 | 12/1992 |
| DE | 3832028 A1 | 3/1990 |
| EP | 0 134 436 A1 | 3/1985 |
| EP | 0085957 B1 | 12/1986 |

(Continued)

OTHER PUBLICATIONS

International Search Report for International Application No. PCT/IB03/02281.
Kitamoto et al., "Suppression of thrombin formation during hemodialysis with triglyceride," *ASAIO Journal* (1993), pp. M581-M583.
Kitamoto et al., "Interaction of Blood and Air in Venous Line Air Trap Chamber," Artifical Organs, vol. 14, Suppl. 4 (1991), pp. 230-232.

Primary Examiner—Duane S Smith
Assistant Examiner—Douglas J Theisen
(74) Attorney, Agent, or Firm—Finnegan, Henderson, Farabow, Garrett & Dunner L.L.P.

(57) ABSTRACT

A description is given of a gas separation device for a physiological fluid, comprising a containing body (6) having at least a first inlet aperture (7) for a physiological fluid, positioned with a tangential direction of access, at least one outlet aperture (9) for the said fluid, spaced apart from the said inlet aperture, and a guide element (17) housed within the said body. The guide element (17) has a continuous active surface (15) designed to contact and guide the said fluid and delimits, together with the containing body (6), a first annular chamber (20) into which the first inlet aperture (7) opens directly.

62 Claims, 3 Drawing Sheets

U.S. PATENT DOCUMENTS

| | | | |
|---|---|---|---|
| 3,909,045 A | 9/1975 | Meagher | |
| 3,939,078 A | 2/1976 | Servas et al. | |
| 3,964,479 A | 6/1976 | Boag et al. | |
| 3,967,620 A | 7/1976 | Noiles | |
| 3,993,062 A | 11/1976 | Jess | |
| 4,009,107 A | 2/1977 | Miller et al. | |
| 4,030,495 A | 6/1977 | Virag | |
| 4,083,706 A | 4/1978 | Wiley | |
| 4,190,426 A | 2/1980 | Ruschke | |
| 4,198,971 A | 4/1980 | Noiles | |
| 4,227,525 A | 10/1980 | Lundquist | |
| 4,231,871 A | 11/1980 | Lipps et al. | |
| 4,256,105 A | 3/1981 | Leahey et al. | |
| 4,263,808 A | 4/1981 | Bellotti et al. | |
| 4,293,413 A | 10/1981 | Schnell | |
| 4,324,662 A | 4/1982 | Schnell | |
| 4,331,540 A | 5/1982 | Witsoe | |
| 4,379,452 A | 4/1983 | DeVries | |
| 4,424,009 A | 1/1984 | van Os | |
| 4,447,230 A | 5/1984 | Gula et al. | |
| 4,492,531 A | 1/1985 | Kenji et al. | |
| 4,526,515 A | 7/1985 | DeVries | |
| 4,534,757 A | 8/1985 | Geller | |
| 4,559,034 A | 12/1985 | Kirita et al. | |
| 4,568,330 A | 2/1986 | Kujawski et al. | |
| 4,568,366 A | 2/1986 | Frederick et al. | |
| 4,571,244 A | 2/1986 | Knighton | |
| 4,572,724 A | 2/1986 | Rosenberg et al. | |
| 4,623,333 A | 11/1986 | Fried | |
| 4,637,813 A | 1/1987 | DeVries | |
| 4,643,713 A | 2/1987 | Viitala | |
| 4,650,454 A | 3/1987 | Moll | |
| 4,662,906 A | 5/1987 | Matkovich et al. | |
| 4,664,800 A | 5/1987 | Raines et al. | |
| 4,758,225 A | 7/1988 | Cox et al. | |
| 4,806,135 A * | 2/1989 | Siposs | 96/212 |
| 4,871,012 A | 10/1989 | Kuo | |
| 4,886,431 A | 12/1989 | Soderquist et al. | |
| 4,900,308 A | 2/1990 | Verkaart | |
| 4,932,987 A * | 6/1990 | Molina | 96/212 |
| 4,950,245 A | 8/1990 | Brown et al. | |
| 5,120,303 A | 6/1992 | Hombrouckx | |
| 5,126,054 A | 6/1992 | Matkovich | |
| 5,154,712 A | 10/1992 | Herweck et al. | |
| 5,421,815 A | 6/1995 | Noguchi et al. | |
| 5,427,509 A | 6/1995 | Chapman et al. | |
| 5,462,416 A | 10/1995 | Dennehey et al. | |
| 5,482,440 A | 1/1996 | Dennehey et al. | |
| 5,578,070 A | 11/1996 | Utterberg | |
| 5,591,251 A | 1/1997 | Brugger | |
| 5,609,571 A | 3/1997 | Buckberg et al. | |
| 5,632,894 A | 5/1997 | White et al. | |
| 5,641,144 A | 6/1997 | Hendrickson et al. | |
| 5,643,205 A | 7/1997 | Utterberg | |
| 5,645,734 A | 7/1997 | Kenley et al. | |
| 5,667,485 A | 9/1997 | Lindsay | |
| 5,674,199 A | 10/1997 | Brugger | |
| 5,674,397 A | 10/1997 | Pawlak et al. | |
| 5,690,821 A | 11/1997 | Kenley et al. | |
| 5,705,060 A * | 1/1998 | Robberts | 210/198.1 |
| 5,707,431 A * | 1/1998 | Verkaart et al. | 96/177 |
| 5,714,060 A | 2/1998 | Kenley et al. | |
| 5,824,212 A * | 10/1998 | Brockhoff | 210/194 |
| 5,849,065 A | 12/1998 | Wojke | |
| 5,863,421 A | 1/1999 | Peter, Jr. et al. | |
| 5,871,693 A | 2/1999 | Lindsay | |
| 5,895,368 A | 4/1999 | Utterberg | |
| 5,935,093 A | 8/1999 | Elgas et al. | |
| 5,961,700 A | 10/1999 | Oliver | |
| 5,980,741 A | 11/1999 | Schnell et al. | |
| 5,983,947 A | 11/1999 | Utterberg | |
| 6,010,623 A | 1/2000 | Schnell et al. | |
| 6,019,824 A | 2/2000 | Schnell | |
| 6,071,269 A | 6/2000 | Schnell et al. | |
| 6,117,342 A | 9/2000 | Schnell et al. | |
| 6,171,484 B1 | 1/2001 | Schnell et al. | |
| 6,176,903 B1 | 1/2001 | Wamsiedler | |
| 6,193,689 B1 | 2/2001 | Woodard | |
| 6,206,954 B1 | 3/2001 | Schnell et al. | |
| 6,251,291 B1 | 6/2001 | Lamphere et al. | |
| 6,277,277 B1 | 8/2001 | Jacobi et al. | |
| 6,308,721 B1 | 10/2001 | Bock et al. | |
| 6,325,775 B1 | 12/2001 | Thom et al. | |
| 6,328,789 B1 | 12/2001 | Spranger | |
| 6,383,158 B1 | 5/2002 | Utterberg et al. | |
| 6,827,862 B1 * | 12/2004 | Brockhoff et al. | 210/787 |

FOREIGN PATENT DOCUMENTS

| | | |
|---|---|---|
| EP | 0128556 B1 | 8/1989 |
| EP | 0354597 A2 | 2/1990 |
| EP | 0376168 A2 | 7/1990 |
| EP | 0 116 596 B1 | 11/1990 |
| EP | 0 282 539 B1 | 1/1992 |
| EP | 0568275 B1 | 11/1993 |
| EP | 0355456 B1 | 1/1995 |
| EP | 0646380 B1 | 4/1995 |
| EP | 0655255 A1 | 5/1995 |
| EP | 0661063 A1 | 7/1995 |
| EP | 0676213 A2 | 10/1995 |
| EP | 0728509 B1 | 8/1996 |
| EP | 0552096 B1 | 10/1996 |
| EP | 0744181 A2 | 11/1996 |
| EP | 0778031 B1 | 6/1997 |
| EP | 0800839 A2 | 10/1997 |
| EP | 0 643 808 B1 | 1/1998 |
| EP | 0 852 953 A2 | 7/1998 |
| EP | 0 695 397 B1 | 9/1998 |
| EP | 0876822 B1 | 11/1998 |
| EP | 0876822 B1 * | 11/1998 |
| EP | 0 887 100 A1 | 12/1998 |
| EP | 0 694 125 B1 | 2/1999 |
| EP | 0 686 237 B1 | 5/1999 |
| EP | 1 084 722 | 3/2001 |
| EP | 1084722 A2 * | 3/2001 |
| EP | 0 679 099 B1 | 7/2001 |
| EP | 0 893 603 B1 | 10/2002 |
| FR | 2508319 | 12/1982 |
| GB | 1 506 555 | 4/1978 |
| GB | 2 076 476 A | 12/1981 |
| GB | 2 208 896 A | 4/1989 |
| GB | 2246713 A | 2/1992 |
| WO | WO 88/01895 | 3/1988 |
| WO | WO-90/11812 | 10/1990 |
| WO | WO-95/06506 | 3/1995 |
| WO | WO 95/17597 | 6/1995 |
| WO | WO 95/17598 | 6/1995 |
| WO | WO 95/17599 | 6/1995 |
| WO | WO 95/17600 | 6/1995 |
| WO | WO 95/17601 | 6/1995 |
| WO | WO 95/17602 | 6/1995 |
| WO | WO 95/17603 | 6/1995 |
| WO | WO 95/17604 | 6/1995 |
| WO | WO 97/02056 | 1/1997 |
| WO | WO 97/10436 | 3/1997 |
| WO | WO-97/41904 | 11/1997 |
| WO | WO 98/22163 | 5/1998 |
| WO | WO-99/22840 | 5/1999 |
| WO | WO-00/32104 | 6/2000 |
| WO | WO 01/08722 A2 | 2/2001 |
| WO | WO-01/30417 A1 | 5/2001 |
| WO | WO 02/26288 A2 | 4/2002 |

* cited by examiner

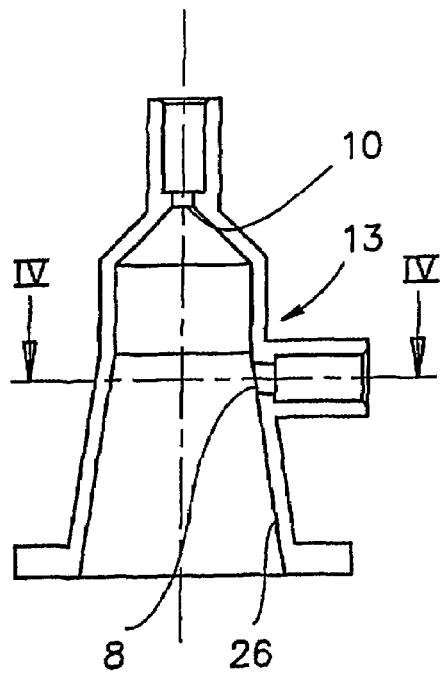
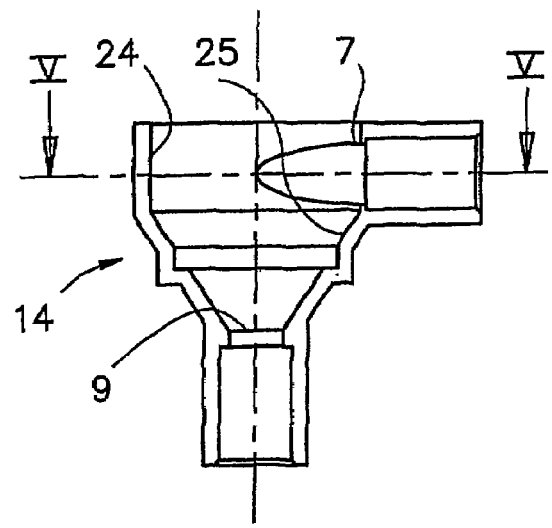
Fig. 2
Fig. 3
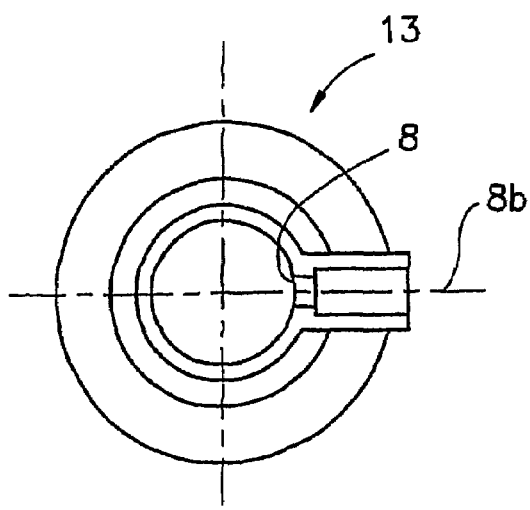
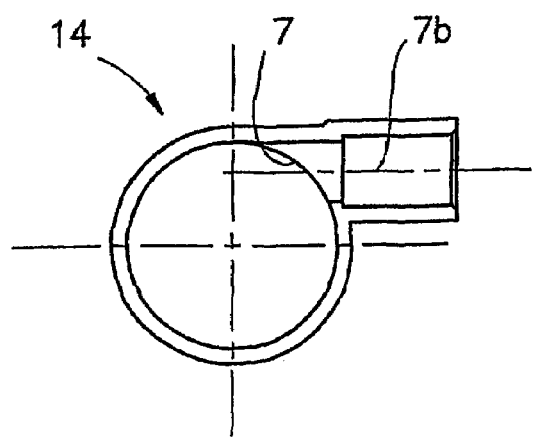
Fig. 4
Fig. 5

GAS SEPARATION DEVICES

BACKGROUND OF THE INVENTION

The present invention relates to a gas separation device for physiological fluids, particularly for cellular fluids such as blood. The present invention relates also to a fluid mixing device with gas separation.

It is known that any gas particles present in a physiological fluid, such as blood circulating in an extracorporeal circuit, must be effectively removed when the fluid is to be administered to a patient. It should be pointed out that this is because excessively large gas particles can be dangerous if they are transferred to a patient's cardiovascular system.

It is also known that some treatments require the simultaneous administration to a patient of both a physiological fluid, for example blood circulating in an extracorporeal circuit, and an additional fluid, for example an infusion or replacement liquid. However, before the two fluids, for example blood and infusion liquid, are transferred to the patient, it is necessary to remove any gas particles that may be present.

This document makes reference, without restrictive intent, to the field of machines for extracorporeal blood treatment, such as dialysis machines, in which field there is a known method of using at least one gas separation device operating in a line for the return of blood to the patient.

A gas separation device suitable for the application described above comprises, typically, a containing body providing within itself a chamber designed to be partially occupied by the blood which is to undergo the degassing operation. Suitable shaping of the chamber allows the blood to accumulate in a lower part of the chamber, thus promoting the separation of the gas bubbles. These bubbles can be removed through a service line or discharged directly to the exterior.

Normally, the pressure within the separation device is kept below atmospheric pressure, in order to promote the separation of the air bubbles.

The blood leaving the device described above then passes through an air bubble sensor which, in turn, can operate a safety clamp. The clamp is typically positioned on the line returning the blood to the patient, in order to prevent any event considered to be dangerous from being propagated into the patient's cardiovascular system.

Another gas separation device of a known type is illustrated in U.S. Pat. No. 5,707,431. This device comprises a cylindrical chamber divided radially into two parts by a filter, also cylindrical, located centrally in the chamber.

The blood inlet is located in a top part of the chamber and is directed tangentially towards the outer part of the chamber to create a vortex flow. The vortex flow of blood in the outer part of the chamber is converted to an essentially vertical flow as a result of the passage of the fluid through the cylindrical filter. The blood proceeds downwards and passes out through an aperture in the lower part of the separation chamber.

The air bubbles, which because of the vortex motion of the blood tend to move towards a perimetric area of the chamber, move upwards towards a hydrophobic membrane which is located at the top of the chamber and which allows the gas to be discharged to the external atmosphere.

Finally, a one-way valve located next to the membrane prevents the air from returning into the chamber.

The following publications:
FR 2,508,319;
EP 0 661 063;
U.S. Pat. No. 5,421,815;
JP 90-182404;

"Interaction of blood and air in venous line air trap chamber", extract from Artificial Organs (vol. 14, suppl. 4), K. Ota and T. Agishi, ICAOT Press, Cleveland 1991, pp. 230-232; and ASAIO Journal (1993), "Suppression of thrombin formation during hemodialysis with triglyceride"

disclose the use of a layer of fluid interposed between the free surface of the blood and the air, in order to reduce the appearance of coagulation phenomena.

In particular, EP 0 661 063 and U.S. Pat. No. 5,421,815 illustrate a blood/air separation chamber comprising a tubular containing body provided with a top cover to which a blood inlet tube is connected. In the described chamber, the blood accumulates in a lower part of the tubular body; in order to separate the blood from direct contact with the air, a static layer of anticoagulant material is used, comprising triglyceride acids and an antioxidant interposed between the free surface of the blood and the air. Since this static layer is carried on the surface and is only miscible with difficulty with the blood, it prevents direct contact between the blood and the air.

Finally, document WO 00/32104 discloses a pressure sensing system in which a service tube, partially filled with a cell-free solution, is interposed between a pressure sensor and a blood circuit. The cell-free solution creates a separating column between the blood and air which, because of the small section of the service tube, prevents or reduces to a minimum the propagation of one or more components of the blood towards the end of the service tube which is occupied by the air.

The technical solutions described above have been found to have certain aspects that could be improved.

In the first place, many of the devices mentioned have large blood-air interfaces which, as is known, promote the formation of clots and encrustations, or, alternatively, in solutions using a static layer to separate the air from the blood, require the use of chemical substances immiscible with blood which float on the surface of the blood to prevent its direct contact with the air.

In the second place, the devices mentioned are not capable of both efficiently mixing the blood with any infusion or replacement fluid that may be present and simultaneously and effectively degassing both fluids.

It should also be noted that the conventional solutions require the presence of a relatively high volume within the gas separation device; in the case of dialysis treatment, for example, the quantity of blood constantly occupying the interior of the separation device increases to a considerable and undesired extent the total amount of blood kept outside the patient.

It should also be noted that, if a tangential blood inlet is to be used to create a vortex to promote the separation of air bubbles from the blood according to the known method, it is necessary to have a central filter to prevent the transfer of the air bubbles to the exit of the separator. The presence of the filter not only increases the overall cost of the device, but also constitutes an additional element which may lead to encrustation and undesired deposits of particles, particularly when part of the filter is located in an air-blood interface area.

Moreover, the known devices which have been described are relatively unsuitable for permitting high blood flows (of the order of 500 ml/min.), low pressure drops and absence of stagnation points, with simultaneous and effective mixing of any infusion liquid.

SUMMARY OF THE INVENTION

The object of the present invention is to provide a gas separation device for a physiological fluid, for example blood, which is capable of operating effectively even at high flow rates, while minimizing the total volume of blood that is to be held within the said device.

A further object of the invention is to provide an optimal quality of the flow through the gas separation device, by essentially eliminating the presence of stagnation points and reducing pressure drops to a minimum.

Another object of the invention is a gas separation device made in such a way that the flow leaving the said device is not capable of generating undesired phenomena of return of gas bubbles towards the outlet of the device.

Another object of the invention is to provide a gas separation device capable of offering an optimal area for access by at least one infusion line, thus permitting an efficient mixing of the blood with the infusion fluid while carrying out effective and simultaneous separation of any gas from the infusion fluid and from the blood, and while minimizing the air-blood interface.

A further object of the present invention is to provide a fluid mixing device with gas separation, capable of operating effectively even at high flow rates, while minimizing the air-blood interface.

The invention also has the object of reducing to the smallest possible level the total volume of blood occupying the said device.

Another object of the invention is to provide a device for actively adjusting the thickness of a layer of infusion liquid lying above the blood or other cellular fluid.

The objects outlined above are essentially achieved by a device according to one or more of the attached claims.

BRIEF DESCRIPTION OF THE DRAWINGS

Further characteristics and advantages will be demonstrated by the detailed description of a preferred, but not exclusive, embodiment of a device according to the present invention.

This description is given below, with reference to the attached drawings, provided purely for guidance and therefore without restrictive intent, in which:

FIG. 2 shows a longitudinal section through an upper half of the containing body of the device according to the invention;

FIG. 3 shows a longitudinal section through a lower half of the containing body of the device according to the invention;

FIG. 4 is a view through the line IV-IV in FIG. 2;

FIG. 5 is a view through the line V-V in FIG. 3;

DETAILED DESCRIPTION

Figures 1, 7:
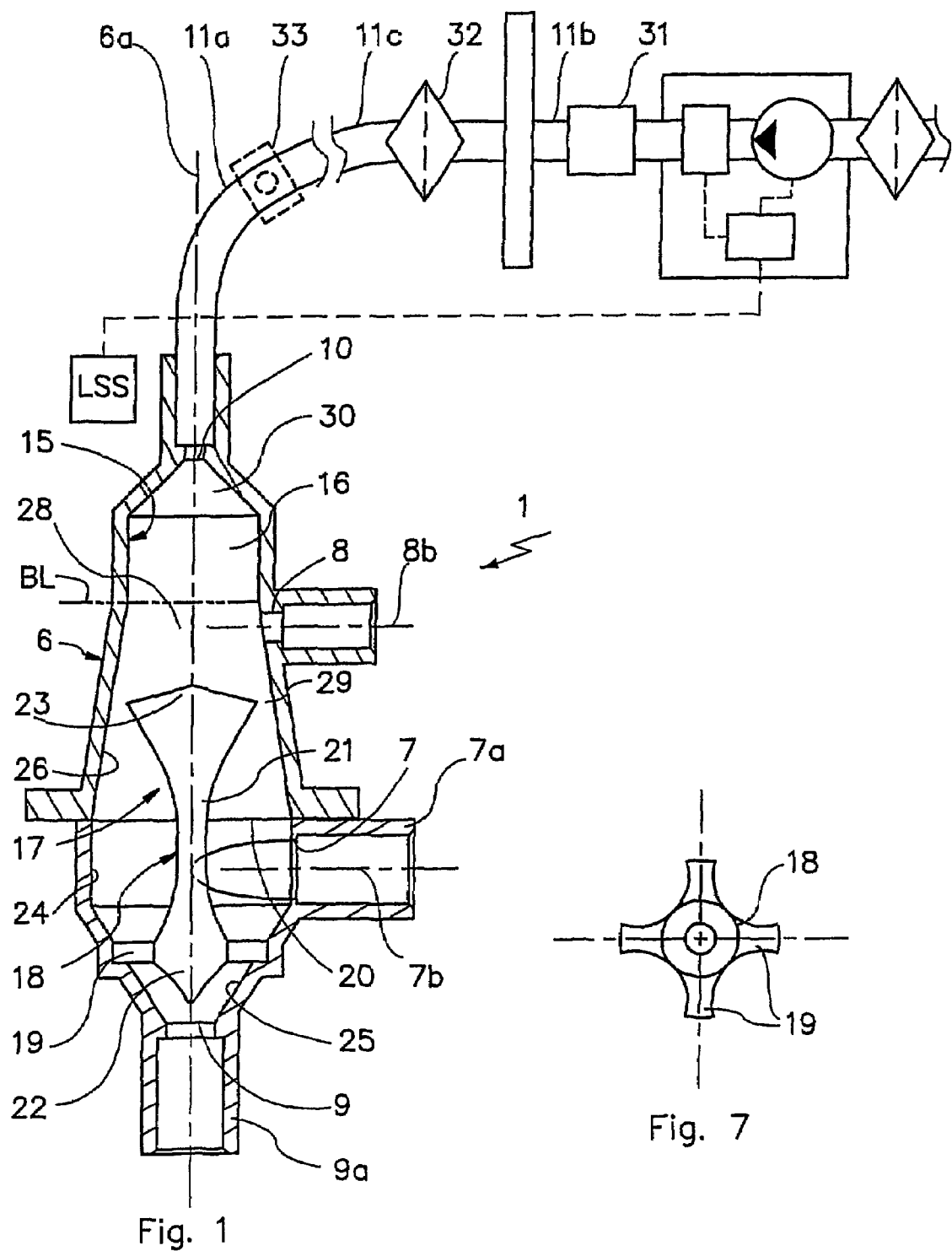
FIG. 1 is a view in longitudinal section, showing the device according to the invention in a vertical position similar to that in which it is used.
FIG. 7 shows a plan view of a detail of FIG. 1.

With reference to FIG. 1, the number 1 indicates a fluid mixing device with gas separation.

Figure 6:
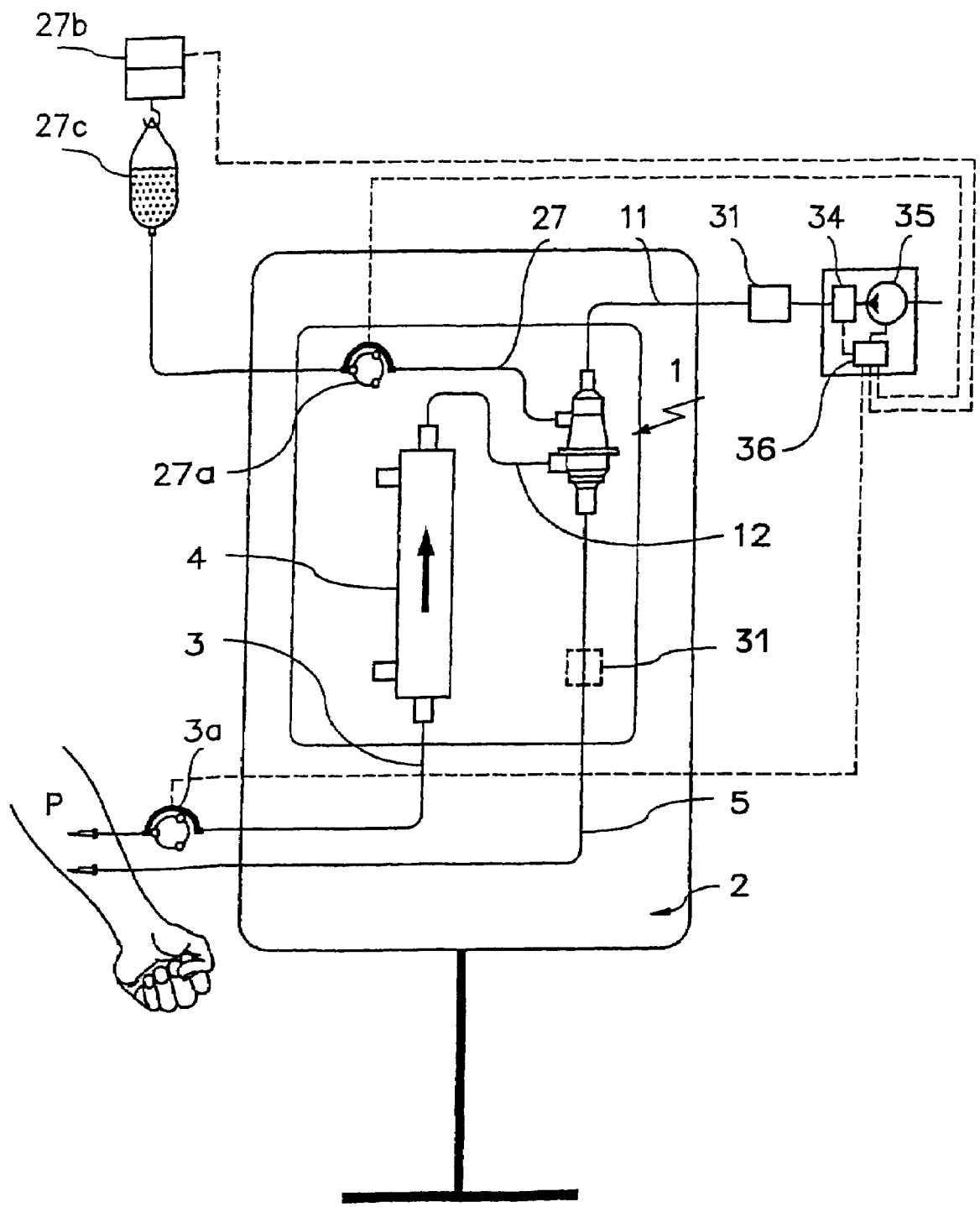
FIG. 6 shows a blood treatment line using the device according to the invention.
Figure 6:
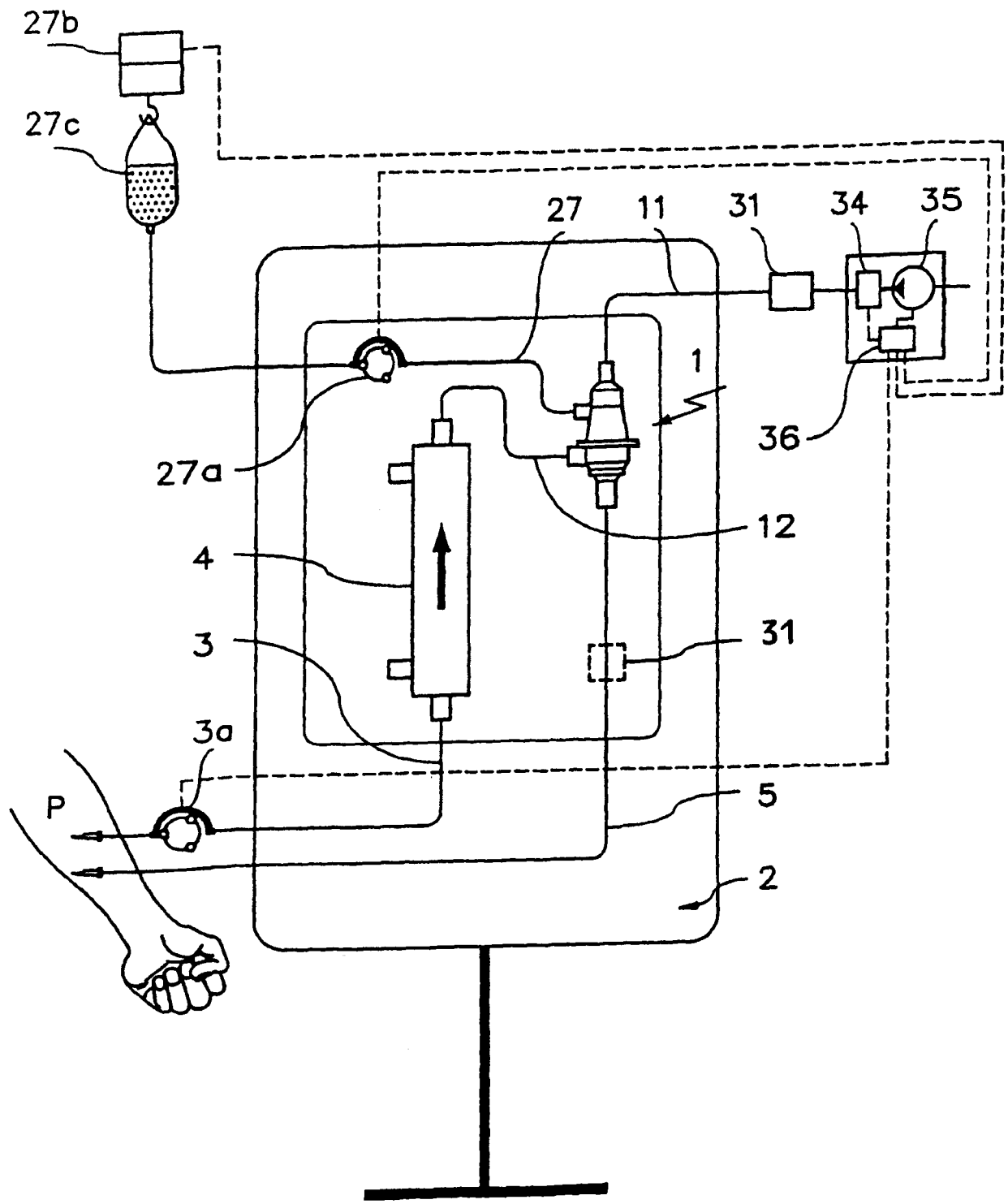

As shown in FIG. 6, the device 1 can operate in a disposable line 2 for extracorporeal blood treatment, comprising a branch 3 for withdrawing the blood from the patient, a blood treatment unit 4 and a branch 5 for returning the blood to the patient.

In greater detail, the unit 4, a dialysis filter for example, is interposed between the two branches 3 and 5, while the device 1 operates on the return branch 5, up-line from the point of access to the patient's vascular system.

The device 1 comprises a containing body 6, having a longitudinal axis of symmetry 6a; the body 6 forms an internal volume 16 which is designed to receive a specified quantity of fluid and which has a radial dimension significantly larger than that of the branches 3 and 5, so that the velocity of the said fluid is decreased and the gas is efficiently separated, as described below.

In operating conditions, both the device 1 and the treatment 4 are positioned with their longitudinal axes orientated vertically, although the device can in fact operate with its longitudinal axis inclined.

The fluid, for example blood, flowing through the line 3 passes through the unit 4 with a vertical upward motion and then enters the device 1 and is returned to the patient, as a result of which an optimal degassing of the liquid is achieved.

The containing body 6 has four apertures: a first inlet aperture 7 for the physiological fluid from which the gas is to be separated, a second inlet aperture 8 designed to convey an infusion fluid into the containing body, an outlet or discharge aperture 9 from which the physiological fluid and any infusion fluid can pass out, and a fourth aperture 10 designed to be connected to a service line 11 for acquiring pressure information, or to be connected directly to the external atmosphere.

In greater detail, the first inlet aperture 7 is formed by a tubular element 7a which communicates with the interior of the containing body and to which a tube 12 for conveying the physiological fluid can be fixed; the first inlet aperture 7 and the corresponding tubular portion 7a are positioned tangentially to the containing body.

The second inlet aperture 8 is spaced apart from and located above the first inlet aperture 7. It should be noted that the second inlet aperture is directed centrally towards the axis 6a of the containing body 6.

The discharge aperture 9, formed by a tubular channel 9a located at the lower end of the containing body, permits the progressive discharge of the blood, or of the blood mixed with the infusion liquid if required.

The containing body 6, whose structure is formed from two halves 13, 14 assembled together, has an active surface 15 which delimits its internal volume 16 where a guide element 17 operates.

The guide element 17 has its own active surface 18, with a continuous profile designed to contact and guide the fluid, as described in detail below. In practice, the guide element is a solid or internally hollow solid of rotation, designed to reduce the internal volume of the containing body that can be actually occupied by the fluid entering through the aforesaid apertures; the guide element 17 is fixed to the said body 6 by means of a support structure comprising radial supports 19 (see FIG. 7), spaced apart at equal angular intervals, interposed between the guide element and the containing body. The guide element extends coaxially with the body 6 and is placed above and spaced axially apart from the discharge aperture 9.

A first chamber 20, which has an essentially annular profile and into which the first inlet aperture opens directly, is thus formed between the active surface 18 of the guide element and the active surface 15 of the containing body.

The active surfaces 15 and 18 of the said containing body and the said guide element face each other and are shaped in the form of surfaces of revolution about a common axis of symmetry which is transverse with respect to the tangential direction of access of the said flow. The geometrical configuration and the relative positions of the active surfaces 15 and 18, combined with the tangential direction of the first access aperture, produce a rotary motion of the blood entering from the first aperture 7 around the guide element. This rotary motion promotes the centrifugal radial movement of the gas bubbles having a relatively low mass (<10 microliters), while the larger bubbles tend to accumulate in the proximity of the surface of the guide element, whose profile tends to make them move upwards towards the aperture 10.

It should be noted that the guide element 17 comprises, in detail, a central portion 21, a first terminal portion 22 facing the said discharge aperture, and a second terminal portion 23 axially opposed to the first terminal portion. The first terminal portion 22 has a cross section whose radial dimension is reduced progressively towards the said discharge aperture: in the illustrated example, the first portion is conical with its vertex facing the discharge aperture; and the second terminal portion 23 has a cross section whose radial dimension is reduced progressively away from the said discharge aperture.

In the illustrated example, the second terminal portion is also conically shaped with its vertex facing away from the discharge aperture; the central portion 21 has a cross section whose radial dimension is reduced progressively away from the said terminal portions, to form an intermediate area having a minimum radial dimension. More precisely, the central portion has a curved profile in longitudinal section. It is this special configuration of the central portion that makes the gas bubbles accumulating on the element 17 tend to rise along a path that essentially follows the profile of the said guide element.

In other words, the guide element has a cross section with a constant profile (preferably circular) whose radial dimension first increases and then decreases from the centre of the element towards the two axially opposed ends, thus forming the aforesaid conical terminal portions 22, 23.

The geometry of the containing body 6 will now be described.

In FIG. 1 it will be noted that the active surface 15 of the body 6 is divided axially into a plurality of consecutive areas. A first area 24, having the maximum radial dimension and a constant radius, extends around the central portion 21 of the guide element. A second area 25, whose radial dimension is reduced progressively towards the discharge aperture, extends consecutively to the first area 24 and essentially around the first terminal portion of the guide element. A third area 26 whose radial dimension is reduced progressively away from the discharge aperture extends consecutively to the first area and essentially around the second terminal portion of the guide element, at the opposite end from the second area.

As is clearly shown in the attached figures, the first inlet aperture opens into the said first chamber 20, in the said first area 24; thus the entering fluid follows a circular path and is effectively decelerated.

Because of the guide element 17, the flow in the first chamber rotates about the axis of the containing body, without being allowed to enter the central area of the said first chamber 20, and without giving rise to areas in which the flow velocity is zero. The absence of stagnation points and zero-velocity areas advantageously prevents the development of a siphon effect towards the discharge outlet, thus preventing a harmful return of bubbles and a practically uncontrolled motion of the fluid.

As mentioned above, the containing body also comprises a second inlet aperture 8 located above the first inlet aperture 7 and connected to a line 27 designed to carry a second fluid into the containing body. Normally, an infusion fluid can be sent through the aforesaid line 27 and introduced into the containing body to mix the fluid with the blood or other physiological fluid.

In particular, the containing body has at least a second chamber 28 located above the guide element, in an axially consecutive position and in fluid communication with the said first chamber 20 via an annular passage 29.

The second inlet aperture 8 opens directly into the said second chamber, and creates a layer of infusion liquid which extends above and in contact with the physiological fluid.

It should be noted that the second aperture is positioned with a direction of access 7*b* which is parallel to the direction of access 8*b* of the first aperture 8. In greater detail, as shown in FIGS. 4 and 5, the directions 7*b* and 8*b* are parallel but staggered, or in other words are located in vertical planes which are spaced apart from each other.

A mixing interface is thus formed between the physiological fluid, such as blood, present in the first chamber and the infusion liquid entering the second chamber.

The uniform and rapid mixing, and the simultaneous degassing, of the two fluids are clearly promoted by the rotary motion imparted to the physiological fluid, by the relative positioning of the corresponding apertures 7 and 8, and by the interaction between the containing body and the guide element.

Moreover, direct contact between the air and the physiological fluid occupying the first chamber is prevented by the provision of a layer of infusion liquid in the second chamber.

In the illustrated case, if the blood or other physiological fluid flows at a rate of approximately 450 ml/min through the first aperture and a saline fluid flows at a rate of 1 ml/min through the second aperture, it is possible to produce a constant saline-blood layer with a thickness of 5-10 mm in the second chamber.

The thickness of the said layer is greater than 2 mm and smaller than the maximum diameter of the internal surface of the containing body, in order to combine effective de-airing with optimal mixing of the fluids; in the case considered here, the maximum thickness is 20 mm.

The supply of fluid along the line 27 is regulated by means of a pump 27*a* controlled by a control unit 36. The unit 36 is programmed to control the pump 27*a* and to provide a specified rate of flow for each specified time interval, in either continuous or intermittent mode. In other words, the control unit can be programmed to follow a specified constant flow rate, or a flow rate variable with time according to a specified profile, or, finally, to supply specified volumes of fluid in intermittent mode at specified time intervals.

A device for measuring the actual flow through the line 27 interacts with the control unit 36. This measuring device comprises, for example, a weighing machine 27*b* designed to weigh a container of liquid 27*c* and to send to the unit 36 information relating to the actual weight of the container during the treatment. Alternatively, a flowmeter interacting with the said control unit can be provided.

The control unit is capable of controlling the flow rate of the blood pump 3*a* and the infusion pump 27*a* in order to ensure that a layer of infusion liquid whose thickness falls within a specified range is constantly present and is located above the blood.

Finally, the containing body includes a third chamber 30, axially consecutive to the said second chamber, and designed to hold and recover the gas separated from the said fluids; the third chamber extends in the top of the containing body, above the theoretical liquid level BL.

In the illustrated example, the third chamber 30 is bell-shaped and its theoretical volume is delimited below by the level BL and above by the fourth aperture, which connects the internal volume of the containing body, and particularly that of the third chamber 30, to a service line or directly to the external environment.

In the illustrated example, a service line 11 is provided, with a first end 11a placed in fluid communication with the said third chamber 30, and a second end 11b connected for operation to a pressure sensor element 31.

As an alternative to what is described above, the pressure sensor element 31 can be made to operate down-line from the device 1.

At least one hydrophobic membrane 32 is associated for operation with an intermediate area 11c of the service line to prevent the access of liquid to the pressure sensor (if present) and to ensure sterile separation between the machine side and the side in which the physiological fluid is present and circulates.

The third chamber has a volume such that any increase in pressure in a range from a minimum value to a maximum value of pressure (from 100 to 350 mmHg, for example) does not cause any penetration of liquid into the service line 11, but instead leaves a constant gas space in the third chamber.

It should be noted that different operating modes can be provided to control the level of the gas that is progressively separated from the fluids or that reaches the device 1 in any way.

1—Fully Manual Mode.

At least one access site 33 can be provided in the service line 11, to enable a user to draw off gas in a fully manual way (by means of a syringe).

2—Semiautomatic Mode.

The service line 11 is connected to the pressure sensor 31, which is connected down-line to a solenoid valve 34 and to an air pump 35. The valve and the pump can be used to send gas to, or to draw gas from, the service line. If the operating level of the liquid to be maintained in the containing body is indicated by BL, the user can control the pneumatic pump and valve circuit, using a keypad for example, to move the level in one or other direction until BL is reached.

3—Automatic Mode.

For operation in fully automatic mode, use is made of a liquid level sensor LLS, of the optical, ultrasonic or other type for example. The sensor LLS is located above the level BL. The level sensor LLS can operate at or near the top of the containing body; alternatively, the level sensor LLS can be made to operate in a section of the tubing 11a, for example in a terminal area of the tubing, essentially next to the fourth aperture 10 as shown in FIG. 1. A control unit 36 is connected to the sensor LLS and operates the pump 35 and the solenoid valve 34, in order to maintain the liquid level in the vicinity of BL. In greater detail, the control unit can order the execution of the following steps:

if LLS signals the presence of liquid:

a) activation of the pump 35 to drive towards the third chamber a volume $V_1$, equal to the volume between LLS and the fourth aperture;

b) activation of the pump 35 to draw gas from the third chamber while LLS continues to signal the presence of liquid;

c) activation of the pump 35 to drive towards the third chamber a volume of liquid $V_2$, equal to $V_1+V_c$, where $V_c$ is the volume of the third chamber.

if LLS does not signal the presence of liquid, then the aforementioned three steps a), b) and c) are repeated automatically in succession at specified time intervals.

It should be noted that the automatic procedure described above has the significant advantage of not allowing liquid to remain stationary in the section in which the sensor LLS operates. This is rather important because the upper layer of liquid, even in the presence of a saline infusion injected through the second aperture, always contains a certain percentage of cellular material which, in the long term, can generate encrustations which adversely affect the correct operation of the sensor LLS and consequently the efficient monitoring of the liquid level.

It should also be noted that the described level monitoring procedure prevents the flow of liquid towards the service line 11, thus providing a further means of ensuring safety and guaranteeing the absolute sterility of the fluid present in the device 1.

The invention claimed is:

1. A gas separation device for a physiological fluid, comprising:
    a containing body having an internal active surface, at least one first inlet aperture for a physiological fluid positioned with a tangential direction of access, and at least one outlet aperture for said fluid spaced apart from said first inlet aperture; said containing body having:
    a guide element housed at least partially within said containing body, said guide element having a continuous active surface configured to contact and guide said fluid, said guide element further comprising:
        a first terminal portion configured to face towards said outlet aperture;
        a second terminal portion axially opposed to the first terminal portion, said second terminal portion configured to face towards a second chamber extending above said guide element; and
        a central portion having a cross section with a radial dimension that is reduced progressively away from said first and second terminal portions, to form an intermediate area having a minimum radial dimension; and
    a first annular chamber formed between the active surface of said guide element and the internal active surface of said containing body.

2. A device according to claim 1, wherein said inlet aperture opens directly into said first chamber.

3. A device according to claim 1, wherein said guide element is wholly housed within the containing body, extends coaxially with the containing body, and is spaced axially apart from said outlet aperture.

4. A device according to claim 3, wherein the internal active surface of said containing body and the active surface of said guide element face each other and are shaped in the form of surfaces of revolution about a common axis of symmetry, said common axis of symmetry being transverse with respect to the tangential direction of access of said flow.

5. A device according to claim 1, wherein said outlet aperture is positioned in a lower end of said containing body, said guide element and said first chamber extending above said outlet aperture.

6. A device according to claim 1, wherein said guide element is a solid or internally hollow solid of rotation, configured to reduce the volume of at least said first chamber.

7. A gas separation device for a physiological fluid, comprising:
a containing body having an internal active surface, at least one first inlet aperture for a physiological fluid positioned with a tangential direction of access, and at least one outlet aperture for said fluid spaced apart from said first inlet aperture; said containing body having:
a guide element housed at least partially within said containing body, said guide element having a continuous active surface configured to contact and guide said fluid; said guide element further comprising:
a central portion;
a first terminal portion configured to face towards said outlet aperture, said first terminal portion having a cross section whose radial dimension is reduced progressively towards said outlet aperture, and wherein said first terminal portion has a conical shape, said first terminal portion having a vertex configured to face towards the outlet aperture; and
a second terminal portion axially opposed to the first terminal portion, said second terminal portion configured to face towards a second chamber extending above said guide element; and
a first annular chamber formed between the active surface of said guide element and the internal active surface of said containing body.

8. A device according to claim 1, wherein the second terminal portion has a cross section whose radial dimension is reduced progressively away from said outlet aperture.

9. A device according to claim 8, wherein the second terminal portion has a conical shape, said second terminal portion having a vertex opposed to the outlet aperture.

10. A device according to claim 1, wherein the central portion has a curved profile in longitudinal section.

11. A gas separation device for a physiological fluid, comprising:
a containing body having an internal active surface, at least one first inlet aperture for a physiological fluid positioned with a tangential direction of access, and at least one outlet aperture for said fluid spaced apart from said first inlet aperture, wherein said internal active surface of the containing body has:
a first area, of maximum radial dimension, extending around the central portion of the guide element;
a second area, whose radial dimension is reduced progressively towards the outlet aperture, the second area extending consecutively to the first area and substantially around the first terminal portion of the guide element; and
a third area, whose radial dimension is reduced progressively away from the outlet aperture, the third area extending consecutively to the first area and essentially around the second terminal portion of the guide element;
wherein said containing body comprises:
a guide element housed at least partially within said containing body, said guide element having a continuous active surface configured to contact and guide said fluid; said guide element further comprising:
a central portion;
a first terminal portion configured to face towards said outlet aperture;
a second terminal portion axially opposed to the first terminal portion, said second terminal portion configured to face towards a second chamber extending above said guide element; and
a first annular chamber formed between the active surface of said guide element and the internal active surface of said containing body, wherein the first inlet aperture opens into said first annular chamber in said first area of the internal active surface of the containing body.

12. A device according to claim 11, wherein the first area of the active surface has a constant radius.

13. A gas separation device for a physiological fluid, comprising:
a containing body having an internal active surface, at least one first inlet aperture for a first physiological fluid positioned with a tangential direction of access, and at least one outlet aperture for said first physiological fluid spaced apart from said first inlet aperture; said containing body having:
a guide element housed at least partially within said containing body, said guide element having a continuous active surface configured to contact and guide said first physiological fluid;
a first annular chamber formed between the active surface of said guide element and the internal active surface of said containing body; and
a second inlet aperture located above said first inlet aperture, said second inlet aperture being configured to convey a second physiological fluid into the containing body.

14. A device according to claim 13, further comprising a second chamber extending above said guide element in an axially consecutive position, said second chamber being in fluid communication with said first chamber and said second inlet aperture.

15. A device according to claim 14, wherein said second inlet aperture opens directly into said second chamber in a direction parallel to, and staggered with respect to, that of said first inlet aperture.

16. A device according to claim 14, wherein said containing body includes a third chamber being axially consecutive to said second chamber, said third chamber being configured to contain the gas separated from the first and second physiological fluids, and to extend in the top of said containing body.

17. A device according to claim 16, further comprising at least one service line having a first end in fluid communication with said third chamber by means of a fourth aperture formed in said containing body.

18. A device according to claim 17, further comprising at least one pressure sensor element associated for operation with said service line.

19. A device according to claim 17, further comprising at least one hydrophobic membrane associated for operation with an intermediate area of the service line.

20. A device according to claim 17, wherein the third chamber has a nominal volume $V_c$ delimited below by a theoretical maximum level line BL and above by said fourth aperture.

21. A device according to claim 17, further comprising a pneumatic circuit operating in said service line for selectively sending gas to the service line and drawing gas from the service line.

22. A device according to claim 21, further comprising a liquid level sensor LLS located above a level BL, and a control unit connected to the sensor LLS and configured to control said pneumatic circuit to maintain the liquid level in the vicinity of said level BL.

23. A device according to claim 22, wherein the level sensor LLS operates in a section of the service line and said control unit is configured to cause the execution of the following steps:
- determining whether LLS is signalling the presence of liquid, and, if so, executing the following sub-steps in sequence:
  - a) activation of the pneumatic circuit to drive towards the third chamber a volume $V_1$ equal to the volume between the section in which LLS operates and the fourth aperture,
  - b) activation of the pneumatic circuit to draw gas from the third chamber while LLS continues to signal the presence of liquid, and
  - c) activation of the pneumatic circuit to drive towards the third chamber a volume of liquid $V_2$, equal to $V_1+V_c$, where $V_c$ is the volume of the third chamber;
- if, on the other hand, LLS is not signalling the presence of liquid, executing the aforementioned three steps a), b) and c) at specified time intervals.

24. A device according to claim 17, further comprising at least one access site located in said service line for manually drawing fluid from said line or sending fluid into said line.

25. A device according to claim 22, wherein the level sensor LLS can operate on said containing body.

26. A gas separation device for a physiological fluid, comprising:
- a containing body having an internal active surface, at least one first inlet aperture for a physiological fluid positioned with a tangential direction of access, and at least one outlet aperture for said fluid spaced apart from said first inlet aperture; said containing body having:
  - a guide element housed at least partially within said containing body, said guide element having a continuous active surface configured to contact and guide said fluid; and
  - a first annular chamber formed between the active surface of said guide element and the internal active surface of said containing body;
- said gas separation device further comprising:
  - a first line for sending the physiological fluid into said containing body through the first inlet aperture,
  - a second line for sending a second fluid into said containing body through a second inlet aperture,
  - a first pump operating to create a flow along the first line,
  - a second pump operating to create a flow along the second line, and
  - a control unit programmed to control the first and second pumps operating in the first and second lines and to ensure the constant presence in the containing body of a layer of said second fluid having a thickness that lies within a specified range, said layer being located above the physiological fluid.

27. A fluid mixing device with gas separation, comprising a containing body having an internal active surface and having at least one first inlet aperture for a first physiological fluid, and at least one fluid outlet aperture, spaced apart from said first inlet aperture, wherein the containing body has at least one second inlet aperture located above said first inlet aperture, said second inlet aperture being configured to convey a second fluid into the containing body to form a layer of said second fluid above said physiological fluid.

28. A device according to claim 27, wherein said containing body includes:
- at least a first chamber extending in a lower area of the containing body and in fluid communication with said outlet aperture;
- at least a second chamber, extending in an axially consecutive upper area and in fluid communication with said first chamber.

29. A device according to claim 28, wherein said containing body includes a third chamber being axially consecutive to said second chamber, said third chamber being configured to contain the gas separated from the first physiological fluid and the second fluid, and extending in the top of said containing body and having a fourth aperture.

30. A device according to claim 29, further comprising at least one service line having a first end in fluid communication with said third chamber by means of the fourth aperture formed in said containing body.

31. A device according to claim 30, further comprising at least one pressure sensor element associated for operation with said service line.

32. A device according to claim 31, further comprising at least one hydrophobic membrane associated for operation with an intermediate area of the service line, between the fourth aperture and the pressure sensor element.

33. A device according to claim 29, wherein the third chamber has a nominal volume V delimited below by a theoretical maximum level line BL and above by said fourth aperture.

34. A device according to claim 30, further comprising a pneumatic circuit for selectively sending gas to the service line and drawing gas from the service line.

35. A device according to claim 34, further comprising a liquid level sensor LLS located above a level BL, and a control unit connected to the sensor LLS and configured to control said pneumatic circuit to maintain the liquid level in the vicinity of said level BL.

36. A device according to claim 35, wherein said level sensor is located in said service line and said control unit is configured to cause the execution of the following steps:
- determining whether LLS is signalling the presence of liquid, and, if so, executing the following sub-steps in sequence:
  - a) activation of the pneumatic circuit to drive towards the third chamber a volume $V_1$, equal to the volume between the section in which LSS operates and the fourth aperture,
  - b) activation of the pneumatic circuit to draw gas from the third chamber while LSS continues to signal the presence of liquid,
  - c) activation of the pneumatic circuit to drive towards the third chamber a volume of liquid $V_2$, equal to $V_1+V_c$, where $V_c$ is the volume of the third chamber;
- if, on the other hand, LLS is not signalling the presence of liquid, executing the aforementioned three steps a), b) and c) at specified time intervals.

37. A device according to claim 30, further comprising at least one access site located in said service line for manually drawing fluid from the service line or sending fluid to the service line.

38. A device according to claim 35, wherein the level sensor LLS operates on the said containing body.

39. A device according to claim 27, further comprising:
- a first line for sending the physiological fluid into said containing body through the first inlet aperture,
- a second line for sending the second fluid into said containing body through the second inlet aperture,
- a first pump operating to create a flow along the first line,
- a second pump operating to create a flow along the second line,
- a programmable control unit for controlling the first and second pumps operating in the first and second lines and for ensuring the constant presence in the containing body of a layer whose thickness lies within a specified range, said layer being located above the first physiological fluid.

40. A device according to claim 39, wherein the control unit activates the second pump operating in the said second line in a continuous or intermittent mode to provide a specified flow rate at every specified time interval.

41. A device according to claim 39, further comprising a means for sensing the actual flow in the second line, said sensing means sending corresponding signals to said control unit.

42. A device according to claim 39, wherein the thickness of the said layer is smaller than the maximum diameter of the internal surface of the containing body.

43. A device according to claim 28, wherein said first inlet aperture opens directly into said first chamber in a tangential direction of access, and said second inlet aperture opens directly towards said second chamber in a direction of access parallel to that of said first aperture.

44. A device according to claim 43, further comprising a guide element housed at least partially within said body and having a continuous active surface designed to contact and guide said first physiological fluid, said first chamber having an annular configuration and being formed between the active surface of said element and the active surface of the containing body.

45. A device according to claim 44, wherein said guide element is wholly housed within the containing body, extends coaxially with the containing body, and is spaced axially apart from said outlet aperture.

46. A device according to claim 44, wherein the internal active surface of said containing body and the active surface of said guide element face each other and are shaped in the form of surfaces of revolution about a common axis of symmetry being transverse with respect to the tangential direction of access of said flow.

47. A device according to claim 44, wherein said outlet aperture is positioned in a lower end of said containing body, said guide element and said first chamber extending above said outlet aperture.

48. A device according to claim 46, wherein said guide element is a solid or internally hollow solid of rotation configured to reduce the volume of at least said first chamber.

49. A device according to claim 44, wherein said guide element comprises:
   a central portion;
   a first terminal portion, facing towards said outlet aperture; and
   a second terminal portion, axially opposed to the first terminal portion and facing towards said second chamber.

50. A device according to claim 49, wherein the first terminal portion has a cross section whose radial dimension is reduced progressively towards said outlet aperture.

51. A device according to claim 50, wherein said first terminal portion has a conical shape, said first terminal portion having a vertex facing towards the outlet aperture.

52. A device according to claim 49, wherein the second terminal portion has a cross section whose radial dimension is reduced progressively away from said outlet aperture.

53. A device according to claim 52, wherein said second terminal portion has a conical shape, said second terminal portion having a vertex opposed to the outlet aperture.

54. A device according to claim 49, wherein the central portion has a cross section with a radial dimension that is reduced progressively away from said first and second terminal portions to form an intermediate area having a minimum radial dimension.

55. A device according to claim 54, wherein the central portion has a curved profile in longitudinal section.

56. A device according to claim 49, wherein said active surface of the containing body has:
   a first area, of maximum radial dimension, extending around the central portion of the guide element;
   a second area, whose radial dimension is reduced progressively towards the outlet aperture, the second area extending consecutively to the first area and essentially around the first terminal portion of the guide element; and
   a third area, whose radial dimension is reduced progressively away from the outlet aperture, the third area extending consecutively to the first area and essentially around the second terminal portion of the guide element.

57. A device according to claim 56, wherein the first inlet aperture opens into the said first chamber, in said intermediate first area.

58. A device according to claim 56, wherein the first area of the active surface of the containing body has a constant radius.

59. A fluid mixing method with gas separation, comprising the following steps:
   providing a containing body having an internal active surface and having at least a first inlet aperture, at least one fluid outlet aperture spaced apart from said first inlet aperture, and at least a second inlet aperture located above said first inlet aperture;
   sending a first physiological fluid into the containing body through said first aperture;
   conveying a second fluid into the containing body through said second aperture to form a layer of said second fluid above said first physiological fluid;
   conveying a separated gas from said first physiological fluid and said second fluid above said layer.

60. A method according to claim 59, further comprising the steps of:
   measuring the flow rate of said first physiological fluid;
   measuring the flow rate of said second fluid;
   regulating the flow rate of said first physiological fluid and said second fluid to provide a layer of said second fluid with a thickness lying within a specified range.

61. A method according to claim 60, wherein said second fluid is sent, in continuous or intermittent mode, in a direction of access to the containing body parallel to that of said first physiological fluid.

62. A method according to claim 60, wherein the thickness of said layer is kept below the maximum diameter of the internal surface of the containing body.

* * * * *

UNITED STATES PATENT AND TRADEMARK OFFICE
CERTIFICATE OF CORRECTION

PATENT NO. : 7,517,387 B2
APPLICATION NO. : 10/518787
DATED : April 14, 2009
INVENTOR(S) : Jacques Chevallet et al.

It is certified that error appears in the above-identified patent and that said Letters Patent is hereby corrected as shown below:

On the title page, item (57), line 2, "body (6) having" should read --body having--.

On the title page, item (57), line 3, "aperture (7) for" should read --aperture for--.

On the title page, item (57), line 5, "aperture (9) for" should read --aperture for--.

On the title page, item (57), line 6, "element (17) housed" should read --element housed--.

On the title page, item (57), line 7, "element (17) has" should read --element has--.

On the title page, item (57), lines 7-8, "surface (15) designed" should read --surface designed--.

On the title page, item (57), line 9, "body (6), a" should read --body, a--.

On the title page, item (57), lines 9-10, "chamber (20) into" should read --chamber into--.

On the title page, item (57), line 10, "aperture (7) opens" should read --aperture opens--.

In the drawing illustrative figure 6 should be deleted to be replaced with the attached figure 6. In the drawing figure 6 should be replaced with the corrected figure 6, as shown on the attached page.

In claim 42, column 13, line 14, "of the said" should read --of said--.

In claim 57, column 14, line 25, "into the said" should read --into said--.

Signed and Sealed this
Twentieth Day of September, 2011

David J. Kappos
*Director of the United States Patent and Trademark Office*